United States Patent [19]

Haynes

[11] Patent Number: 4,697,584
[45] Date of Patent: Oct. 6, 1987

[54] DEVICE AND METHOD FOR PLUGGING AN INTRAMEDULLARY BONE CANAL

[75] Inventor: Darrel W. Haynes, 3804 Offutt Rd., Randallstown, Md. 21133

[73] Assignee: Darrel W. Haynes, Randallstown, Md.

[21] Appl. No.: 659,975

[22] Filed: Oct. 12, 1984

[51] Int. Cl.⁴ ............................................... A61F 5/04
[52] U.S. Cl. ............................... 128/92 VQ; 128/325; 128/344
[58] Field of Search ..................... 128/325, 344, 92

[56] References Cited

U.S. PATENT DOCUMENTS

| 3,834,394 | 9/1974 | Hunter et al. | 128/325 |
| 3,889,665 | 6/1975 | Ling et al. | 128/92 |
| 3,939,820 | 2/1976 | Grayzel | 128/344 |
| 4,213,461 | 7/1980 | Pevsner | 128/348 |
| 4,245,359 | 1/1981 | Stuhmer | 3/1.9 |
| 4,293,962 | 10/1981 | Fuson | 3/1.9 |
| 4,302,855 | 12/1981 | Swanson | 3/1.9 |
| 4,311,146 | 1/1982 | Wonder | 128/325 |
| 4,327,734 | 5/1982 | White | 128/325 |
| 4,341,218 | 7/1982 | Ü | 128/325 |
| 4,344,190 | 8/1982 | Lee et al. | 3/1.9 |
| 4,357,716 | 11/1982 | Brown | 3/1.913 |
| 4,364,392 | 12/1982 | Strother et al. | 128/325 |
| 4,447,915 | 5/1984 | Weber | 3/1.9 |
| 4,462,394 | 1/1984 | Jacobs | 128/344 |
| 4,471,779 | 9/1984 | Antoshkiw | 128/325 |
| 4,527,549 | 7/1985 | Gabbay | 128/344 |

FOREIGN PATENT DOCUMENTS

| 815863 | 6/1969 | Canada | 128/344 |
| 2637119 | 3/1977 | Fed. Rep. of Germany . | |
| 57-26128 | 6/1982 | Japan . | |

Primary Examiner—Gene Mancene
Assistant Examiner—Wencelao J. Contreras
Attorney, Agent, or Firm—Zegeer, Jim

[57] ABSTRACT

This invention relates to a method of plugging the open end of an intramedullary bone canal with an inflatable bone plug which is capable of restricting the flow of bone cement during the insertion of bone cement, particularly during the pressurized injection of such a cement, during an operative procedure involving the fixation of the stem of an artificial joint prosthesis to the end of a bone such as in the fixation of a hip joint prosthesis to the proximal femur. The inflatable bone plug is inflated with a fluid which is capable of escaping from the plug within a relatively short period of time after the bone cement holding the prosthesis in place has hardened to avoid possible weaking of the cortical bone surrounding the inflated plug. This invention also relates to an inflatable bone plug of the above type which is preferably constructed from a silicone elastomer and is pressurized with carbon dioxide gas.

20 Claims, 10 Drawing Figures

DEVICE AND METHOD FOR PLUGGING AN INTRAMEDULLARY BONE CANAL

BACKGROUND OF THE INVENTION

This invention relates to a method of plugging the open end of an intramedullary bone canal with an inflatable device which is capable of restricting the flow of bone cement, particularly during the pressurized injection of bone cement, during a procedure involving the implantation of a joint prosthesis to the end of a bone. The device is further capable of deflating in a relatively short period of time after the cement hardens to avoid possible weakening of the cortical bone surrounding the inflated device. This invention also relates to the inflatable bone cement restrictor device ("inflatable bone plug") used in such a method.

Degenerative bone diseases and injuries to the joints often make it necessary or desirable to replace the natural joint with an artificial prosthesis One such replacement involves the fixation of an artificial hip joint prosthesis to the proximal end of the femur. The femur contains a hollow intramedullary bone canal running through its central long axis. It is desirable to affix a hip joint prosthesis to the femur in such a manner that the stem of the prosthesis lies along the central long axis of the femur. In preparing the proximal end of the femur to receive such a prosthesis, an appropriately sized opening to receive the stem of the prosthesis is made in the proximal end of the femur. That opening normally extends into the intramedullary bone canal approximately along the central long axis of the femur and is wide enough to permit bone cement to be compacted about the stem to secure the prosthesis to the femur.

To prevent bone cement from flowing deeper into the intramedullary bone canal than is necessary, an intramedullary bone canal plug ("bone plug") composed of a piece of the removed femur or a plug of partially cured bone cement has been used to restrict the flow of cement. Likewise various bone plugs having sides which press-fit against the cortical bone forming the canal to form a seal have been proposed in U.S. Pat. Nos. 4,245,359 (Stuhmer, issued Jan. 20, 1981); 4,302,855 (Swanson, issued Dec. 1, 1981) and 4,293,962 (Fuson, issued Oct. 13, 1981). Press-fit bone plugs are generally designed to be inserted in one direction and have the disadvantage of not always being removable once they are inserted. This can be a disadvantage where the plug has inadvertently been inserted too deeply into the intramedullary bone canal. Another disadvantage of such a plug is evidenced when too large of a size has been selected and the plug can neither be inserted to the proper depth without the use of excessive force nor can it be easily removed.

Since the femur is composed of living tissue which is permeated with blood vessels and tissue fluid, the escape of blood and tissue fluid can result in poor adherence of the bone cement to the femur. For this reason, it has become more common to inject cement into the opening in the proximal femur under pressure to cause the bone cement to permeate into the porous bone structure and thereby obtain better adhesion to the femur. See, for example, U.S. Pat. Nos. 3,889,665 (Ling, et al., issued June 17, 1975), 4,357,716 (Brown, issued Nov. 9, 1982) and 4,462,394 (Jacobs, issued 7/31/84) for examples of such pressurized bone cement injection processes. Press-fit bone plugs have a further disadvantage when used in pressurized injection systems because the pressure can drive the plug down the canal much further than is necessary or desirable.

Use of a very tightly fitting press-fit plug to avoid plug movement has further disadvantages such as causing a change in the flexural rigidity of the cement/bone system as discussed in U.S. Pat. No. 4,344,190 (Lee, et al., issued Aug. 17, 1982). The Lee, et al. Patent notes that change in the flexural rigidity of the cement/bone system can increase the risk of bone fracture at the point where the plug presses against the bone. Lee, et al. state that a fracture at that point is very difficult to set. If a press-fit plug is too large for the intramedullary bone canal opening, a surgeon may not, or may only with great difficulty, be able to remove the plug once it is inserted in the opening. The answer provided by Lee, et al. is to construct a press-fit bone plug of a biodegradable material which is reabsorbed by the body after the cement hardens. The pressure against the bone is thereby relieved by reabsorption after the cement hardens and the risk of a fracture occurring in that area is said to be reduced. No mention is made as to the length of time required before a sufficient level of resorption of the plug occurs to release the pressure. Furthermore, there is no way to adjust to tightness of fit other than by plug size selection. Once inserted, the plug appears to be difficult to remove and, once inserted, a less than optimally-fitting plug could be driven deeper into the canal by the pressure of the cement being injected.

One bone plug designed to be securely fastened inside of the intramedullary bone canal is taught in U.S. Pat. No. 4,447,915 (Weber, issued May 15, 1984). The Weber Patent teaches a two piece medullary bone canal plug formed by a deformable and expandable outer body having a jacket formed of a number of segments and a conical expansion body which is pulled into the outer body to expand the outer body. Once pulled together, the two bodies are permanently secured together via serrations of the inside of the outer body and the outside of the expansion body. However, it appears that once the two bodies are secured together, the plug cannot be removed if for some reason that should become desirable. Likewise, if the plug is secured so that too much pressure is exerted against the sides of the intramedullary bone canal, the presence of the plug may increase the risk of fracture as noted in the Lee, et al. patent above.

There appears to be a need for a bone plug which possesses the following characteristics: (a) it should be capable of being used for a variety of intramedullary bone canal or operative opening sizes in a bone for reception of a joint prosthesis; (b) it should be capable of being tightly secured to a controllable degree against the walls of the canal or opening to restrict the passage of bone cement, particularly cement injected under pressure, past the plug even when the bone plug is placed beyond the isthmus of a bone such as in the femur, (c) it should be capable of being removed after securement against the wall prior to the placement of bone cement into the intramedullary bone canal or opening and (d) it should be capable of releasing the pressure against the wall of the canal or opening in a relatively short period of time after the hardening of the bone cement to decrease the risk of bone resorption and remodelling or changes which could result in fracture of the bone due to stresses on the walls of the canal or opening surrounding the plug. The object of this invention is to provide a bone plug possessing such characteristics and a method for using the same to accomplish the fixation of an artificial joint prosthesis on the end of a bone. In accordance with this invention, this is accomplished through the use of an inflatable bone plug of a biocompatible elastomeric material which is capable of being inflated with a biocompatible fluid to apply a preselected amount of pressure against the walls of the operative opening or intramedullary bone canal and thereby fit tightly into a variety of opening or bone canal diameters. The inflatable bone plug is provided with a means whereby the biocompatible fluid, preferably carbon dioxide gas, used to inflate the plug is retained within the bone plug for a sufficient length of time to prevent the liquid bone cement from passing around the plug and to permit the bone cement to harden. Thereafter, the fluid escapes through a controlled release means from the bone plug and the pressure exerted by the bone plug against the walls is reduced to a minimum.

Miniature detachable balloon catheters which have been used to accomplish the blockage of blood vessels are known and some of these are described in U.S. Pat. Nos. 3,834,394 (Hunter, et al, issued Sept. 10, 1974); 4,311,146 (Wonder, issued Jan. 19, 1982); 4,327,734 (White, issued May 4, 1982); 4,341,218 (Ü, issued July 27, 1982) and 4,364,392 (Strother, et al., issued Dec. 21, 1982). These devices employ a tiny balloon fixed by means of a valve to the end of a long catheter which is passed as a unit through a blood vessel. The balloon is inflated to accomplish blockage of the blood vessel and the catheter is detached. None of these patents suggest plugging the intramedullary bone canal of a bone with such a device. Furthermore, the balloons described therein are generally not intended to deflate by themselves since it would be undesirable to have the balloon released within a vessel as discussed in the White and the Strother, et al. patents. U.S. Pat. No. 4,213,461 (Pevsner, issued July 22, 1980) describes a miniature balloon catheter which has a pin-hole located opposite the cannula to enable a fluid to be dispersed from the site of the pin-hole for diagnostic purposes. The Ling, et al. Patent describes a pressurized cement delivery system which is used to accomplish pressurized cement delivery with an expandable rubber plug, but the plug is not left in the canal to restrict the flow of cement further into the canal after the stem is inserted, but is designed to seal the open end of the femur from outward escape of cement during pressurization. None of these patents suggest the novel method and device which forms the subject matter of this invention.

BRIEF DESCRIPTION OF THE DRAWINGS

The above and other objects, features and advantages of the present invention will become apparent to those skilled in the art upon examination of the following description of the present invention.

In the drawings.

DETAILED DESCRIPTION OF THE INVENTION

Figure 1:
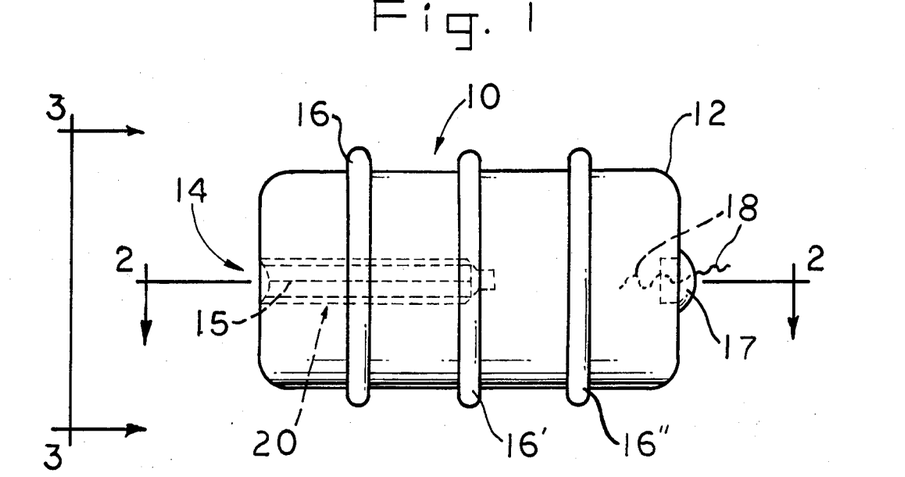
FIG. 1 is a plan view of an inflatable bone plug of the present invention showing the internal components thereof in relief.

Referring to the drawings, FIG. 1 shows one embodiment of the inflatable bone plug 10 of the present invention which is shown as a generally cylindrical, almost barrel-like, container 12 having a valve opening 14 at one end, a series of optional raised ribs 16, 16' and 16" on its outer walls to accomplish better sealing against the walls of the intramedullary bone canal and an end sealing button 17 sealingly fixed to the end by means of an adhesive so that the plug 10 can be inflated with a fluid. An optional filament 18 passes completely through the button 17. Resealable valve 20 and passage 15 passing completely through valve 20 are shown in relief as dotted lines.

Figure 2:
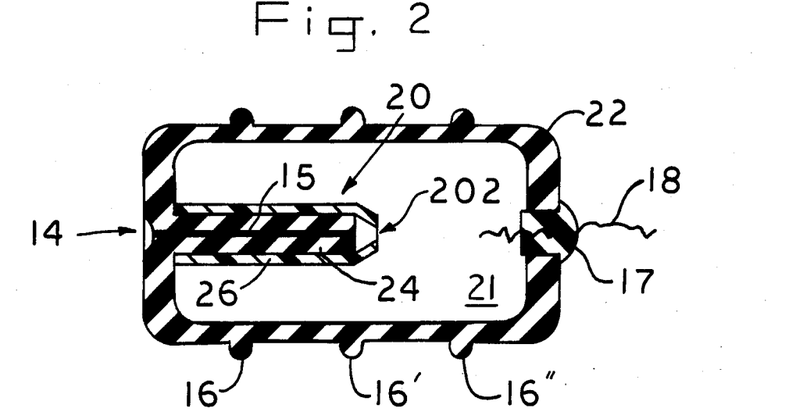
FIG. 2 is a cross-section of the inflatable bone plug of FIG. 1 taken along section lines 2—2.

FIG. 2 more clearly shows the interior region 21 of container 12 in cross-section showing valve opening 14 leading to passage 15 which permits communication between the exterior of container 12 and interior region 21 separated by wall 22 to accomplish pressurization of interior region 21 by injection of a biocompatible fluid. The ends of the container valve 20 and button 17 are slightly thicker than the remaining container walls to cause expansion along the central long axis of the container. Preferably, the container expands within the canal along its central long axis such that after pressurization and inflation, the length of the pressurized container running parallel to the central long axis of the bone canal is at least 2 times its diameter. Resealable valve 20 is simple in construction. A number of resealable valves could be employed in making the inflatable bone plugs of the present invention.

Figure 9:
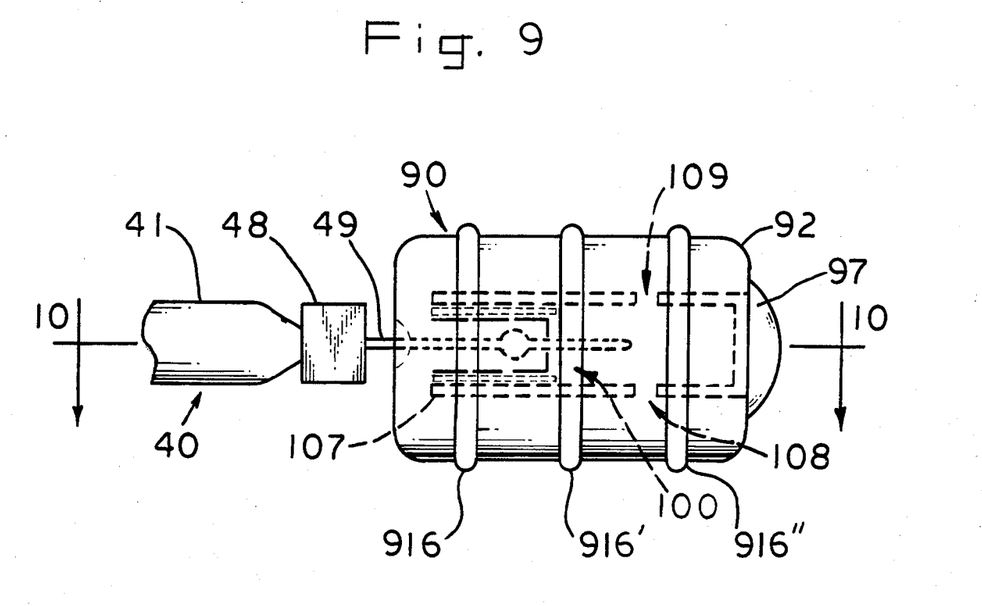
FIG. 9 is a plan view of an alternate embodiment of an inflatable bone plug which contains a central rigidifying rod.
Figure 10:
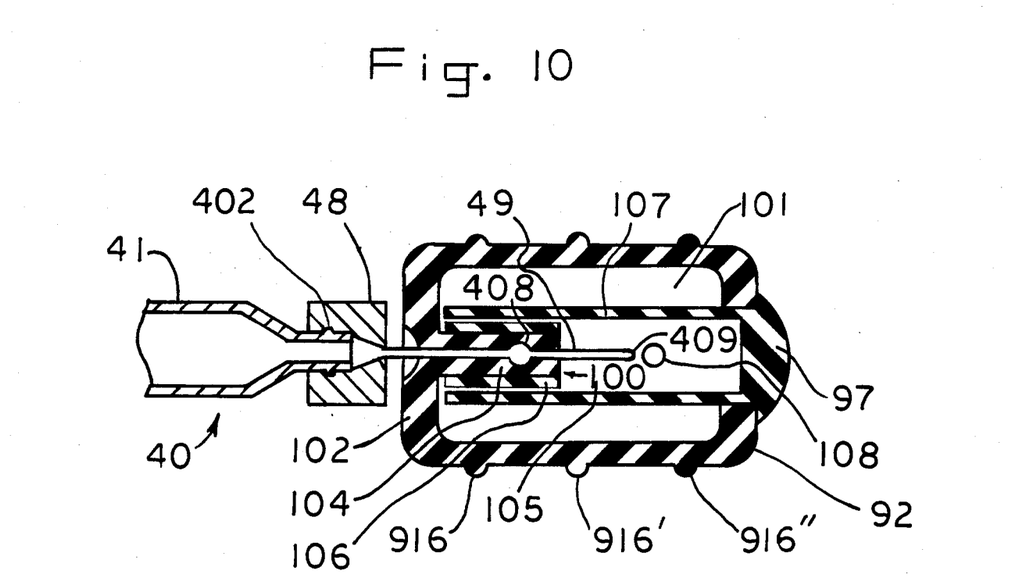
FIG. 10 is a cross-sectional view of the inflatable bone plug of FIG. 9 taken along lines 9—9.

The specific designs of the inflatable bone plug device shown in FIGS. 1-4, which is now the embodiment preferred by me and the other optional embodiment shown in FIGS. 9-10 are the subject of a U.S. patent application Ser. No. 06/659,976 filed concurrently herewith in the name of Eldon E. Frisch entitled "Method Of Making An Intramedullary Bone Plug And Bone Plug Made Thereby" and assigned to the same assignee as the present invention. This Frisch Application is hereby incorporated by reference to teach the production of one type of inflatable bone plug useful in the present invention. In the embodiments shown in FIGS. 1-4 and 9-10, the valve stem 24 is an integral part of the container material 22 itself which is constructed of a biocompatible elastomeric material such as a silicone elastomer or a polyurethane elastomer.

One of the novel features of preferred embodiments of the present invention involves the selection of a container material which is permeable to the biocompatible fluid selected for pressurizing and inflating the container forming the inflatable bone plug. In such a preferred embodiment, at least a portion, and preferably the entire container, is constructed of a material which is sufficiently permeable to the fluid being injected that the fluid will permeate through the material and cause the pressure of the interior region of container 12 to drop to a minimum within 24 hours after pressurization. The container material 22 or permeable portion thereof must not be so permeable to the fluid that the container cannot retain its pressure for a sufficient period of time to allow a surgeon to complete the insertion of the prosthesis stem and to permit the cement to harden. Medical grade silicone elastomers which are commercially available from Dow Corning Corporation, Midland, MI 48640 under the registered trademark "SILASTIC" are one example of biocompatible materials which are useful to form such a container. Examples of other silicone elastomers can be found in the patent literature. Silicone elastomers are preferred and, of those, silicone elastomers having good resistance to tearing are preferred since the exposed bone can abrade the container walls. Examples of fluids which can be used to pressurize the container are carbon dioxide, helium, water or isotonic saline solution with carbon dioxide being most preferred. Fluids that would cause embolisms or other deleterious effects in the body should be avoided. Permeation of nongaseous fluid out of the exterior region 21 can be increased through the addition of optional filament 18 which can be a stainless steel strand or several strands woven together or one or more strands of a porous or non-porous biocompatible material such as DACRON ® polyester. A combination of a container of a substantially polydimethylsiloxane elastomer with carbon dioxide as a pressurizing fluid is presently preferred, based on the inherent high permeability of polydimethylsiloxane elastomer to carbon dioxide as well as its biocompatibility.

Figure 8:
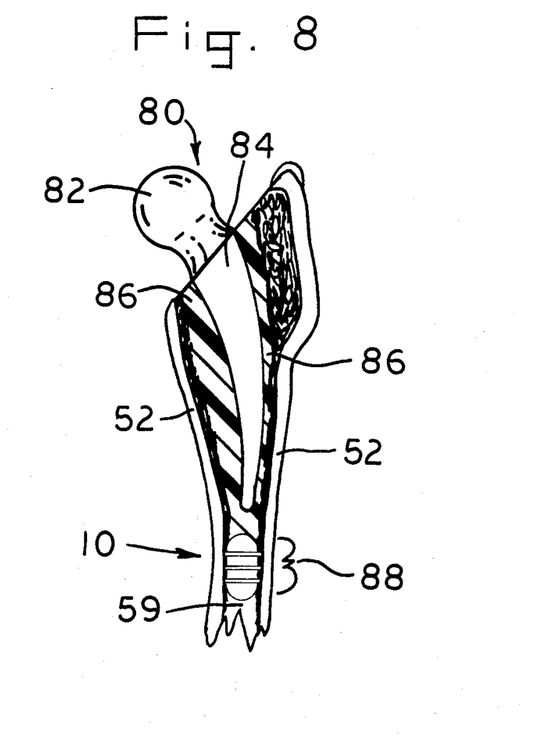
FIG. 8 shows the inflated bone plug in place after the bone cement and prosthesis stem have been inserted into the opening in the femur.

Use of a gaseous fluid permits the container to be constructed in a simpler fashion since the entire container can be made of one material. The container walls should be of a sufficient thickness to be able to contain the pressure within interior region 21 without bursting during inflation and should also be sufficiently thick to prevent puncturing or weakening of the walls upon contact with the bone during insertion into the intramedullary bone canal. Silicone elastomers, particularly polydimethylsiloxane elastomers, are therefore quite suitable for use as a container material since their high permeability permits one to select an appropriate wall thiokness without substantial loss in permeability. This is advantageous because it is an important feature of this invention that the inflated bone plug depressurize and deflate within a relatively short time after the bone cement has hardened to avoid possible weakening of the bone at the point where the plug is implanted in the canal. For example, the container 12 of FIG. 1 can be molded as a whole using conventional molding techniques from a medical grade polydimethylsiloxane elastomer having a Die B tear resistance of at least about 200 p.p.i. per ASTM D624; Shore A durometer of about 30–40 per ASTM D2240; tensile strength at break of at least 900 p.s.i., elongation of at least 500% at break, and a 100% modulus of at least 75 p.s.i. per ASTM D412 in such a manner that the valve stem 24 extends away from the rest of container 12. Passage 15 is prepared by running a needle or other cutting instrument completely through portion 24 and exiting through the wall of container 12 at opening 14. A solvent swellable elastomeric band 26 of silicone elastomer, such as one of the same type of elastomer from which the container 12 is made which may additionally contain a radiopaque filler such as barium sulfate to make the implanted plug visible radiographically, which is of slightly smaller inner diameter than the outer diameter of stem 24 is swollen in solvent so that it can be fitted over stem 24. The solvent is allowed to evaporate so that the band shrinks over stem 24 and seals passage 15 so that a resealable valve 20 now exists on one end of the container 12. Other resealable valve designs can be employed as will be apparent to those skilled in the art; see for example, the valves described in the previously mentioned patents relating to miniaturized balloon catheters. The container is then turned inside out by means of a hole left in container 12 so that valve 20 is now within interior region 21. Opening 202 provides an opening where the tip of needle 49 can extend into region 21. Button 17 is then used to seal the hole in container 12 by means of a silicone or other adhesive material so that interior region 21 can be pressurized. Button 17 can contain optional filament 18 or an optional appropriate diameter passage may be extended through button 17 to permit controlled release of pressure from interior region 21. Another reason that a permeable container is preferred is that if the passage through button 17 or a deflation passage elsewhere on the container 12 is covered by bone upon insertion (i.e., if the container twists on insertion or does not insert as shown in FIG. 8, release of internal pressure may not occur as rapidly as is desirable). This can be minimized by using the embodiment in FIGS. 9 and 10, but it is still preferred that the entire container be permeable to the fluid.

Figure 3:
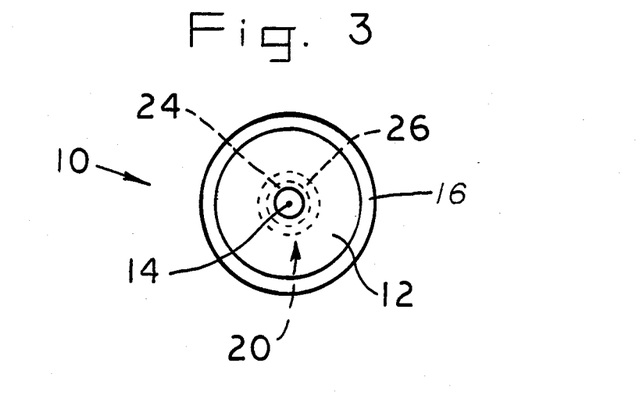
FIG. 3 is an end view of the inflatable bone plug of FIG. 1 as viewed in the direction of arrows 3—3.

FIG. 3 is an end view of plug 10 showing valve opening 14 in container 12 and the relation of internal valve 20 with stem 24 and elastic band 26 (shown in relief as dotted lines) thereto. Opening 14 is slightly concave with passage 15 at the lowest part of the concavity.

Figure 4:
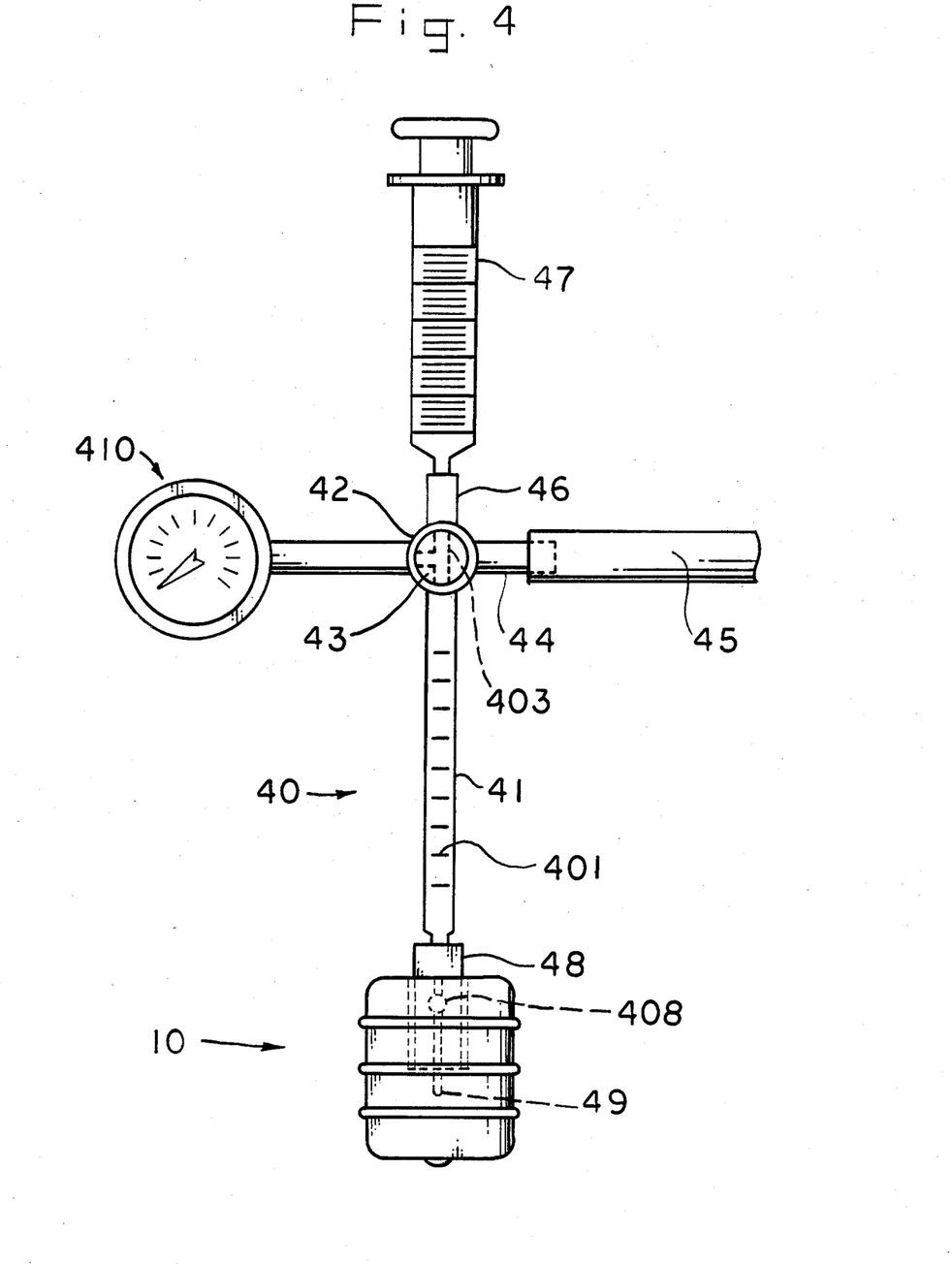
FIG. 4 is a perspective view of an inflatable bone plug of the present invention fitted with a fluid injection device having a hollow needle placed within the valve present on the plug.

FIG. 4 shows plug 10 affixed to a fluid injection device 40 which provides for the measured injection of a preselected quantity of fluid within plug 10. Device 40 consists of a rigid hollow tube having one end in sealing communication with a three-way stopcock 42. In addition to tube 41, stopcock 42 further contains hollow tubes 44 and 46, respectively, all of the interior bases of which are in sealing communication with rotatable insert 43 having passages 403 for selecting which interior bases of tubes 41, 44 and 46 shall be in communication with the others. Tubes 41, 44 and 46 can be made of metal, glass, or some other biocompatible, sterilizable material. Tube 41 may also be bent in a manner which may aid the insertion of the plug into the operative opening and intramedullary bone canal as shown at location 71 in FIG. 7. Tube 41 contains a series of calibration marks 401 to aid the surgeon in placing the bone plug 10 within the intramedullary bone canal at the desired location. Calibrated syringe 47 is in sealing communication with tube 46 and fluid delivery tube 45, which is connected to a source of fluid to be injected into plug 10, is sealingly affixed to tube 44. An optional pressure gauge 410 is sealingly affixed to stopcock 42. The end of tube 41 opposite stopcock 42 is sealingly affixed to a bullet-nosed injection needle 49 which is passed through passage 15 of plug 10 to accomplish pressurization and inflation of plug 10 by means of a connector 48 to which the upper end of needle 49 is also affixed. Needle 49 contains a buttom portion 408 which serves to hold the bone plug on the needle during insertion. Needle 49 and connector 48 are preferably of a rigid material such as stainless steel.

During use, rotatable insert 43 of stopcock 42 is rotated so that passages 403 are brought into alignment with the fluid passing through tube 45 so that syringe 47 and tube 41 can be purged of air and filled with the fluid to be injected. It is preferred that the bone plug be stretched by inflating and deflating several times before insertion to assure proper inflation within the intramedullary bone canal. It is also preferred that the bone plug be deflated as much as possible before insertion to ease insertion and placement in the intramedullary bone canal. Likewise, plug 10 can be purged so that only the fluid to be injected is present in the interior of plug 10. After purging and stretching, the plug is ready for insertion into the intramedullary bone canal.

Figure 5:
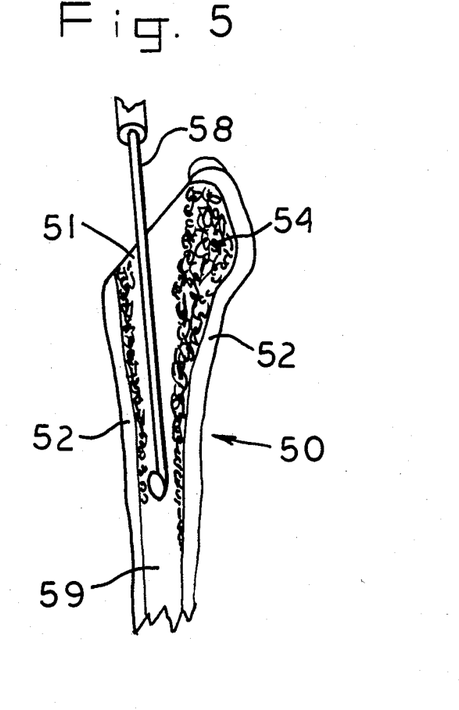
FIG. 5 shows the final stage of the preparation of the proximal end of the femur to receive the stem of an artificial hip joint prosthesis.

FIGS. 5-8 illustrate, in cross-section with all nonessential body structures omitted for clarity, the method of the present invention by showing the fixation of an artificial hip joint prosthesis to the proximal end of the femur. FIG. 5 shows the final stage in the preparation of the proximal end of femur 50. An operative opening 51 in the proximal femur for the reception of the stem of an artificial hip joint prosthesis has been made in accordance with conventional procedures well known to those skilled in the art and does not need to be described herein. FIG. 5 illustrates the use of a suction device 58 to remove debris and fluids from operative opening 51 in femur 52 which has been made through the hard cortical bone 52 and the softer porous bone 54. The opening 51 has been extended such that contact with intramedullary bone canal 59 has been made.

Figure 6:
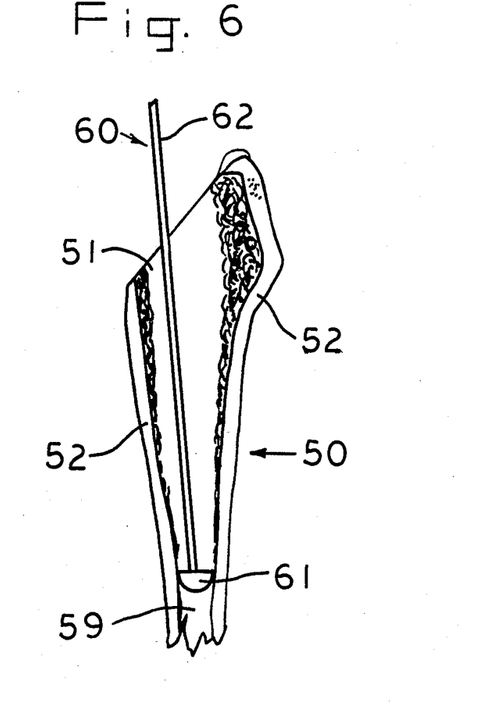
FIG. 6 shows the insertion of a calibrated measuring device into the intramedullary bone canal to determine the amount of fluid to be injected into the plug.

FIG. 6 shows insertion of measuring head 62 of a calibrated measuring device 60 by means of handle 61 into the opening 51 to a depth (depth guide markings can be placed on the handle if desired) which is at least equal to and, preferably slightly greater than, the distance into which the lowest part of the stem of the artificial joint prosthesis is to extend. Measuring head 62 can be made in various sizes so that the measuring head size can be correlated with the quantity of fluid to be injected into the interior region 21 of plug 10 so as to enable a surgeon to properly inflate the plug 10 to sufficient degree to be assured that cement will not be driven past the plug nor will the plug be forced further down the intramedullary bone canal 59. Likewise, overinflation of the plug within the canal can also be avoided. Since the plug 10 expands, a number of operative opening or intramedullary bone canal diameters can be accomodated by one plug size. A polydimethylsiloxane elastomer bone plug which was 20.3 millimeters(mm) (0.8 in.) in length by 11.7 mm (0.46 in.) in diameter was constructed and tested with good results in human cadavers. Measuring head 62 could also be calibrated to a particular level of pressure which can be read from optional gauge 410, thus giving actual feedback to the surgeon as to the level of pressurization of the inflatable bone plug 10 after it is inserted in the canal 59. Since needle 49 is sealingly engagable with valve 20, the pressure can be adjusted or the entire plug 49 can be removed by releasing the pressure within the interior region 21 of plug 10 or if the needle has been removed, it can be reinserted and the foregoing procedure used.

Figure 7:
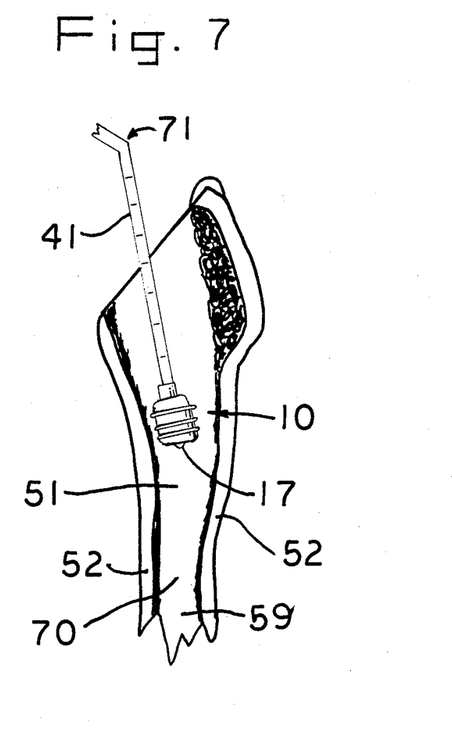
FIG. 7 shows the insertion of the inflatable bone plug of the present invention.

Device 40 can be used as a means for inserting plug 10 with the end bearing button 17 entering first through opening 51 as shown in FIG. 7. Depth markings (not shown) could be placed on tube 41 to enable the surgeon to determine the correct positioning (shown as reference numeral 70 for illustrative purposes) of the plug 10 in canal 59. The plug can then be pressurized and inflated to a preselected level as described previously. Device 40 is retracted leaving plug 10 in place and the opening 51 is filled with bone cement, preferably under pressure, in accordance with conventional techniques. The stem of the artificial joint prosthesis may be inserted before, during or after the introduction of the cement in accordance with well known techniques which form no part of this invention.

FIG. 8 shows artificial hip joint 80 having femoral head 82 and stem 84. Stem 84 is surrounded by bone cement 86 which is allowed to harden and thereby firmly affix stem 84 and thereby prosthesis 80 within the proximal femur. Plug 10 has prevented the advance of cement into canal 59 beyond the plug 10 by virtue of the tight fit of plug 10 against the walls of intramedullary bone canal 59 bounded by bone 52. Plug 10 then loses internal pressure and deflates over a period of time and releases the pressure against the bone 52 shown as region 88 surrounding the plug. Since the bone is living, pressure in region 88 can cause bone resorption or other change in bone character in region 88. Because the inflatable bone plugs of the present invention are manufactured to lose their internal pressure over a period of time, the chance of a fracture in that area as a result of changes in bone structure near such a plug is minimized.

In testing, about 60 ml carbon dioxide gas was placed in a gas syringe of the type shown in FIG. 4 and was used to inflate a bone plug of the present invention to a pressure of about 30 p.s.i. Bone cement was injected into the intramedullary bone canal and allowed to harden to stimulate insertion of a prothesis. Radiographs were taken before and after cement insertion. The bone plug was observed to deflate within about six hours after insertion.

FIGS. 9 and 10 show an alternate design embodiment of an inflatable bone plug useful in the present invention shown as bone plug 90 which partially shows injection device 40 as tube 41 affixed to connector 48 by way of a lock ring 402 and with needle 49 inserted through resealable valve 100 so that bulbous portion 408 holds the needle within the valve 100 and hollow tip 409 extends into hollow space 105 so that fluid injected through needle 49 passes into space 105 which communicates with the hollow interior region 101 of container 92 through apertures 108 and 109 to accomplish pressurization of container 92. Like container 12 of plug 10 shown in FIG. 1, container 92 contains button 97 which seals the end of container 92. Container 92 is constructed in a manner quite similar to that described for container 12 and contains three raised ribs 916, 916' and 916". Valve 100 is constructed in the same manner as that described for valve 20 by creating a passage through the center of valve stem 104 and placing an elastomeric band 106 over the stem which shrinks over stem 104 to form the valve 100. In this embodiment, button 97 has a hollow tubular portion 107 which extends along the central long axis of container 92 from the end of container 92 opposite valve 100 across to fit over valve 100. This configuration of button 97 keeps the plug 92 straighter upon insertion so that there is less chance for the plug to turn sideways upon insertion and possibly lose some ability to form an adequate seal against the sides of the intramedullary bone canal. If desired, the end of portion 107 fitting over valve 100 can also be affixed to band 106 of valve 100 to restrict expansion along the central long axis of plug 92 and cause more pressure to be exerted radially from that axis against the sides of the canal.

While the present invention has been described with reference to the replacement of a hip joint, the technique may find use in the replacement of another joint where it is desirable to restrict the flow of bone cement into an intramedullary bone canal.

Furthermore, other modifications and variations of the inflatable bone plug and method of using the same will become apparent to those skilled in the art from an examination of the above specification and drawings. Thus, other variations of the inflatable bone plug and method of using the same may be made which fall within the scope of the appended claims even though such variations were not specifically discussed above.

That which is claimed is:

1. A method of replacing a diseased or damaged joint with a prosthetic device of the type including a stem fixable within the intramedullary bone canal of an open-ended bone adjacent to the joint, said method comprising the steps of:
    (A) preparing the end of the bone and the intramedullary canal of the bone for receipt of the stem of an artificial joint prosthesis,
    (B) inserting an inflatable bone plug into the canal a distance from the open end of said bone which is at least more than the distance which the stem will be inserted into said canal for cementing to the bone, said plug comprising an expandable container of a biocompatible elastomeric material having an exterior wall configuration which is adapted to be received within said canal and an interior wall enclosing a hollow interior region, said container having a first end fitted with a reealable valve means to enable injection of a biocompatible fluid into said hollow interior means through the use of a further cooperating injection means which is sealingly enageable with said valve means and an opposing second end, said second end being the end which is first inserted into the open end of said canal, said container wall having a sufficient strength and thickness to contain pressure resulting form injection of said fluid, said container further containing a means for the controlled release of said fluid to reduce the pressure therein to a minimum within a preselected amount of time after injection of a pressuring amount of said fluid,
    (C) injecting a preselected quantity of fluid into said interior region through the use of the injection means to raise the pressure of said interior region to a sufficient level to enable the outside wall of the container to sealingly conform to the walls of the intramedullary bone canal surrounding the container,
    (D) removing the injection means,
    (E) inserting a hardenable bone cement material and said stem into said canal, wherein the cement is prevented from flowing beyond said plug as a result of the contact with the canal produced by the pressure of the fluid within said interior region,
    (F) allowing the cement to harden, and
    (G) allowing the pressure within said container to drop to a minimum after the cement has hardened.

2. The method as claimed in claim 1 wherein in Step (F), said bone cement is injected under pressure into the open end of the bone blocked by the plug.

3. The method as claimed in claim 1 which further includes the step of measuring the diameter of the intramedullary bone canal at the location where the plug is to be placed with a calibrated measuring device to determine the quantity of fluid to be injected into the container to achieve a preselected level of pressure within the interior region of the container.

4. The method as claimed in claim 1 wherein said container has a generally cylindrical shape which is constructed to expand within the canal in such a manner that, after being injected with a pressurizing amount of said fluid, the length of the pressurized device running parallel to the central long axis of the canal is at least about 2 times its diameter.

5. The method as claimed in claim 1 wherein the means for controllably releasing the pressure within said internal region comprises a container wherein at least a portion thereof is manufactured from a material through which the fluid injected is capable of permeating in a controlled manner.

6. The method as claimed in claim 5 wherein at least a portion of the container is manufactured from a silicone elastomer and the fluid is selected from the group consisting of carbon dioxide gas and helium gas.

7. The method as claimed in claim 6 wherein the container is manufactured from a polydimethylsiloxane elastomer and the fluid is carbon dioxide gas.

8. The method as claimed in claim 7 which further includes the step of measuring the diameter of the intramedullary bone canal at the location where the plug is to be placed with a calibrated measuring device to determine the quantity of fluid to be injected into the container to achieve the preselected level of pressure within the interior region of the container.

9. The method as claimed in claim 7 wherein said container has a generally cylindrical shape which is constructed to expand within the canal in such a manner that, after being injected with a pressurizing amount of said fluid, the length of the pressurized plug running parallel to the central long axis of the canal is at least about 2 times its diameter.

10. The method as claimed in claim 7 wherein in step (E), the cement is injected under pressure into the open end of the bone blocked by the plug.

11. An inflatable implantable bone plug for plugging an open-ended intramedullary canal of a bone to restrict the flow past said plug of a hardenable bone cement used to fix the stem of an artificial joint prosthesis into the open end of said canal, said plug comprising an expandable container of a biocompatible elastomeric material having an exterior wall configuration which is adapted to be received and implanted within said canal between said stem and the remainder of said intramedullary canal, said outside wall being configured to sealingly conform to the walls of said canal surrounding the container when the container is pressurized to prevent bone cement from passing beyond the plug and entering the remainder of said intramedullary canal, said container having an interior wall enclosing a hollow region, said container having a first end fitted with a resealable valve means to enable injection of a biocompatible fluid into said interior region through the use of a further cooperating and removable injection means which is sealingly engageable with said valve means and which injection means is removed from said valve means before the insertion of said cement and said stem within the open end of said canal and an opposing second end, said second end being the end which is first inserted into the open end of said canal, said container walls having a sufficient strength and thickness to contain pressure from injection of said fluid, said container further containing a means for the controlled release of said fluid into the remainder of said intramedullary canal to reduce the pressure within said interior region to a minimum a preselected amount of time after injection of a pressurizing amount of said fluid and thereby reduce the pressure against the walls of said intramedullary canal surrounding said plug after said cement has hardened.

12. The inflatable bone plug of claim 11 wherein said container has a generally cylindrical shape which is constructed to expand within the canal in such a manner that, after injection of said pressurizing amount of fluid, the length of the pressurized container running parallel to the central long axis of the canal is at least 2 times its length.

13. The inflatable bone plug of claim 11 wherein the means for controllably releasing the pressure within said interior region comprises a container wherein at least a portion thereof is manufactured from a material through which the fluid injected is capable of permeating in a controlled manner.

14. The inflatable bone plug as claimed in claim 13 wherein at least a portion of the container is manufactured from a silicone elastomer and the fluid intended to be injected therein is selected from the group consisting of carbon dioxide gas and helium gas.

15. The inflatable bone plug as claimed in claim 14 wherein the container is manufactured substantially from a polydimethylsiloxane elastomer and the fluid is carbon dioxide gas.

16. The inflatable bone plug as claimed in claim 15 wherein said container has a generally cylindrical shape which is constructed to expand within the canal in such a manner that, after being injected with a pressurizing amount of said fluid, the length of the pressurized plug running parallel to the central long axis of the canal is at least 2 times its diameter.

17. A bone plug for plugging an open-ended intramedullary canal of a bone to restrict the flow past said plug and into said intramedullary canal beyond said plug of a hardenable bone cement to fix the stem of an artificial joint prosthesis, said bone plug comprising an expandable container made from an elastomeric material, said container having an exterior wall which, when said container is expanded sealingly engages and conforms to the interior wall structure of said intramedullary canal of a bone, valve means for receiving injection of a biocompatible fluid under pressure within the interior of said container, and means for controlling the release of said injected fluid into said intramedullary canal to reduce the pressure within the interior of said container, to a minimum preselected amount, within a predetermined time, after injection of the pressuring fluid to thereby remove the pressure by said plug against the interior walls of said intramedullary canal surrounding said plug, after the cement has hardened.

18. The bone plug defined in claim 17 in which said container has a generally cylindrical shape and a length, when inflated, about a central longitudinal axis which is at least 2 times its diameter.

19. The bone plug defined in claim 17 wherein said means for controlling the release of fluid comprises a portion of said container wall remote from the side walls and cement being comprised of a material through which said fluid is capable of permeating in a constricted manner.

20. The bone plug defined in claim 17 wherein said container is polydimethylsiloxane elastomer.

* * * * *